United States Patent [19]

D'Silva

[11] Patent Number: 4,675,340

[45] Date of Patent: Jun. 23, 1987

[54] INSECTICIDAL AND MITICIDAL OXIME N-ALKYL-N-α-HALOACYLCARBAMATE DERIVATIVES, COMPOSITIONS, AND METHOD OF USE THEREFOR

[75] Inventor: Themistocles D. J. D'Silva, Chapel Hill, N.C.

[73] Assignee: Union Carbide Corporation, Danbury, Conn.

[21] Appl. No.: 807,744

[22] Filed: Dec. 11, 1985

Related U.S. Application Data

[62] Division of Ser. No. 509,452, Jun. 30, 1983, Pat. No. 4,576,965.

[51] Int. Cl.$^4$ .................... A61K 31/385; C07D 339/6; C07D 339/8
[52] U.S. Cl. .................................. 514/436; 514/442; 549/21; 549/38
[58] Field of Search .................... 549/21, 38; 514/436, 514/442

[56] References Cited

FOREIGN PATENT DOCUMENTS 1232930  4/1969  United Kingdom ............ 260/545 R

OTHER PUBLICATIONS

Boulton et al, *Pesticide Science*, vol. 2, pp. 10–15.
Nuridzhanyan, K. A. et al., J. Org. Chem., USSR 5, 856–860, (1969).

*Primary Examiner*—John M. Ford
*Assistant Examiner*—J. G. Mullins
*Attorney, Agent, or Firm*—Morgan & Finnegan

[57] ABSTRACT

Pesticidal oxime N-alkyl-N-α-haloacyl-carbamates represented by the structure:

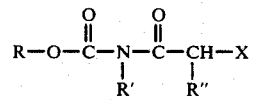

wherein R represents an imino radical, R' and R" represent alkyl radicals and X is chlorine, fluorine or bromine.

7 Claims, No Drawings

INSECTICIDAL AND MITICIDAL OXIME N-ALKYL-N-α-HALOACYLCARBAMATE DERIVATIVES, COMPOSITIONS, AND METHOD OF USE THEREFOR

This application is a division of application 06/509,452, filed 6/30/83, now U.S. Pat. No. 4,596,965.

FIELD OF THE INVENTION

The present invention relates to novel phosphorylated carbamates useful as pesticides. More particularly, the present invention relates to oxime N-alkyl-N-α-haloacylcarbamates useful as the active agents in pesticidal compositions for controlling insects and mites and as intermediates in the synthesis of other insecticides and miticides.

BACKGROUND OF THE INVENTION

British Pat. No. 1,232,930 discloses pesticidal oxime N-acylcarbamates which have the structure:

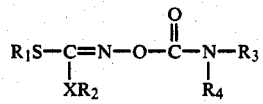

wherein X is an oxygen atom or a covalent bond, $R_1$ and $R_2$ are alkyl, $R_3$ is hydrogen or alkyl and $R_4$ is an optionally substituted acyl such as chloroacetyl. Such compounds were made by reacting an N-chloroacetylisocyanate with an oxime and then alkylating the N-chloroacetylcarbamate with diazomethane.

It was reported by J. J. K. Boulton, et al., in the journal *Pesticide Science*, Vol. 2, pp. 10–15 (1971), that N-acylation of pesticidal oxime carbamates results in an almost total loss of toxicity of these compounds with respect to both insects and mammals.

SUMMARY OF THE INVENTION

The present invention is directed to oxime N-alkyl-N-α-haloacylcarbamates which, contrary to the teaching of Boulton, et al., above, are useful as insecticides and miticides and which can be treated with an alkylthiophosphorothioate salt to form a pesticidally active derivative as disclosed in my copending application Ser. No. (D-13,726), filed [Insert Date] entitled "Pesticidal Oxime N-Alkyl-N-(alkylthio-phosphorothio)acylcarbamates".

This invention is also directed to a novel process for producing such compounds, as well as insecticidal and miticidal compositions comprising an acceptable carrier and a pesticidally effective amount of such compounds, and methods for controlling insects and mites using such compounds.

DETAILED DESCRIPTION OF THE INVENTION

The oxime carbamates of this invention have the structure:

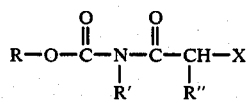

wherein:

$R'$ is $C_{1-4}$ alkyl;
$R''$ is hydrogen or $C_{1-4}$ alkyl;
X is chlorine, fluorine or bromine; and.
R is:

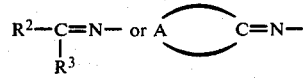

wherein:
$R^2$ is:
(a) $C_{1-6}$ alkyl, $C_{3-6}$ cycloalkyl, or phenyl, all of which may be unsubstituted or substituted with one or more halogen, alkoxy, alkylthio, alkylsulfinyl, alkylsulfonyl, amido, alkoximino, nitro or cyano groups, or
(b) alkoxy, alkoxycarbonyl, cyano, aminocarbonyl, alkylaminocarbonyl, or dialkylaminocarbonyl, provided that R may contain no more than six aliphatic carbon atoms;
$R^3$ is hydrogen, $C_{1-6}$ alkyl, $C_{1-6}$ alkoxy, cyano, alkoximinoalkyl or $C_{1-6}$ alkylthio, except that $R^3$ may not be alkylthio when $R^2$ is alkyl or alkoxy; and
A is a four or five membered, saturated or unsaturated, divalent chain composed of carbon atoms and not more than two atoms selected from the group comprised of nitrogen, oxygen and sulfur atoms, wherein the carbon and nitrogen atoms of said chain may be $C_{1-4}$ alkyl substituted.

The acyclic compounds of the present invention are compounds wherein $R^2$ and $R^3$ may be a variety of hydrocarbon radicals which may be branched or straight chain, substituted or unsubstituted, and saturated or unsaturated. When $R^2$ and $R^3$ are different, the compound is steroisomeric, i.e., it can exist in the E or Z form. If the oxime reactant is a mixture of E and Z stereoisomers, then the oxime carbamate will exhibit similar stereoisomerism. This invention encompasses both stereoisomeric forms of the oxime carbamates as defined by the above formula.

The cyclic compounds are those in which A forms cyclic radicals such as
2-ylidine-1,4-dithiane; 2-ylidine-1,3-dithiane;
4-ylidine-1,3-dithiolane; 2-ylidine-1,3-dithiolane;
2-dicyanomethylidene-4-ylidene-1,3-dithiolane;
2-ylidinethiophane; 4-ylidine-1,3-oxathiolane;
5-ylidine-1,3-thiazolidin-4-one;
2-ylidine-1,3-thiazolidin-4-one;
2-ylidine-tetrahydro-1,4-thiazine;
2-ylidine-4-thiono-1,3-thiazolidin;
2-ylidine-tetrahydro-1,4-thiazin-5-one;
2-ylidine-1,3-thiazoline; 2-ylidine-1,3,5-trithiane,
all of which may be substituted with $C_{1-4}$ alkyl. The term "2-ylidine-" denotes that the doubly bonded nitrogen of the oxime portion of the molecule is bonded to the carbon atom at the number 2 ring position in accordance with accepted heterocyclic nomenclature used by those skilled in the art.

Generally, the preferred compounds are those in which $R'$ is methyl, $R''$ is hydrogen and X is chlorine. Preferred acyclic compounds are those in which $R^2$ is alkyl substituted with alkylthio, alkylsulfinyl, alkylsulfonyl, cyano, nitro or alkoximino and $R^3$ is hydrogen, alkyl or alkoxy. Preferred cyclic compounds are those with a six membered ring containing two sulfur atoms as ring members such as a 1,4-dithianyl ring, or a five membered ring with a sulfur atom as one ring member and a second hetero atom as a second ring member such as a 1,3-oxathiolanyl ring or a 1,3-thioazolidin-4-one ring.

The oxime carbamates of the present invention can be prepared using well established procedures for preparing carbamate derivatives. The preferred method of preparing these compounds is by the novel process outlined below:

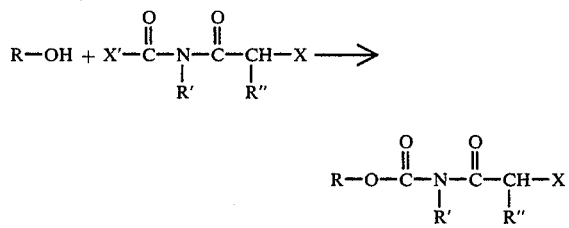

wherein R, R', R", and X are as previously defined: and X' is a reactive halogen such as fluorine or chlorine.

The oxime reactants are available from commercial sources or can be prepared by the convention methods for preparing oximes known to those skilled in the art. The carbamoyl halide reactants above can be prepared by reacting an alkyl isocyanate with an α-haloacyl halide in the presence of a modified anhydrous zinc chloride catalyst. Reagent grade zinc chloride is premixed with silica gel and heated to above about 300° C. This modified zinc chloride should be stored in an anhydrous atmosphere and used under anhydrous conditions. Such a process is more particularly disclosed and claimed in copending application Ser. No. (D-13,720), entitled "Novel N-α-Haloacyl-N-Hydrocarbylcarbamoyl Halides" by C. K. Rao et al., filed (insert date).

Approximately stoichiometrically equivalent amounts of the N-α-haloacylcarbamoyl halide and oxime compounds are reacted in a solvent which is inert under the reaction conditions utilized. Illustrative of such suitable solvents are aromatic hydrocarbons such as toluene, xylene, naphthalene, tetralin; aliphatic chlorinated hydrocarbons such as methylene chloride, chloroform, carbontetrachloride, mono-, di- and tri-chloroethylene; low boiling aliphatic ketones and nitriles such as acetone, methylisobutyl ketone, methylethyl ketone, acetonitrile, propionitrile; and ethers such as diethylether, t-butyl-methyl ether, dioxane and tetrahydrofuran.

The reaction is preferably conducted at ambient temperatures and pressures. However, a wide range of temperatures and pressures, temperatures between about −20° to about 100° C., and pressures above and below atmospheric, can be employed. The reaction is usually conducted under an inert atmosphere, such as nitrogen, with stirring, for a time sufficient to allow the reaction to proceed to completion. The inert nitrogen atmosphere will prevent oxidation of the amine reactant and product that may occur in air.

Examples 1–4 are illustrative of the methods of preparing the compounds of the present invention.

EXAMPLE 1

Preparation of 2-Methyl-2-methylthio-propionaldoxime N-chloroacetyl-N-methylcarbamate To a solution of 5.0 g (0.029 mol) of N-chloroacetyl-N-methylcarbamoyl chloride dissolved in 30 ml of toluene was added slowly with stirring to a mixture of 3.9 g (0.029 mol) of 2-methyl-2-methylthio-propionaldoxime dissolved in 25 ml of toluene and 2.9 g (0.29 mol) of triethylamine. The reaction mixture was stirred at ambient temperature for three days. The salt was removed by filtration and the filtrate was concentrated to yield 6.8 g of light yellow viscous oil which crystallized on standing having a melting point of 32°–33° C.

$C_9H_{15}ClN_2O_3S$: Calcd: C, 40.52, H, 5.67, N, 10.48 Found: C, 40.53; H, 6.05, N, 11.52.

EXAMPLE 2

Preparation of 2-Methyl-2-methylsulfonylpropionaldoxime-N-chloroacetyl-N-methylcarbamate To a solution of 5.0 g (0.029 m) of N-chloroacetyl-N-methylcarbamoyl chloride dissolved in 40 ml of toluene was added 4.74 g (0.029 m) of 2-methyl-2-methylsulfonylpropionaldoxime dissolved in 35 ml. of toluene followed by a slow addition of 2.9 g (0.029 m) of triethylamine. The reaction mixture was stirred at ambient temperatures over a period of 3 days. The solid product was filtered. The filter cake was washed with water and hexane and air dried to afford 5.7 g of a white solid with a melting point of 120°–121° C.

$C_9H_{15}ClN_2O_3S$: Calcd: C, 36.21, H, 5.06, N, 9.37, Found: C, 37.07; H, 5.93, N, 9.41.

EXAMPLE 3

Preparation of 2-Cyano-2-methylpropionaldoxime-N-chloroacetyl-N-methylcarbamate

To a mixture of 3.24 g (0.029 m) of 2-cyano-2-methylpropionaldoxime, 5.0 g (0.029 m) of N-chloroacetyl-N-methylcarbamoyl chloride in 50 ml of toluene was added 2.92 g (0.029 m) of triethylamine. After stirring for 2 hours, the solid was filtered. The filter cake was washed with water and hexane and air dried to afford 5.2 g of a white solid with a melting point of 115° C.

$C_9H_{12}ClN_3O_3$: Calcd: C, 43.99, H, 4.92, N, 17.1, Found: C, 44.43; H, 5.19, N, 16.9.

EXAMPLE 4

Preparation of 1-Ethoxyacetaldoxime-N-chloroacetyl-N-methylcarbamate

To a solution of 5.0 g (0.05 m) of ethyl N-hydroxyacetimidate and 8.5 g (0.05 m) of N-chloroacetyl-N-methyl-carbamoyl chloride dissolved in 75 ml of toluene was added 5.05 g (0.05 m) of triethylamine. After stirring for 2 hours the reaction mixture was filtered through a bed of Celite. The filtrate was concentrated under reduced pressure to afford 10.3 g of a light yellow crystalline solid. m.p. 69°–71° C.

$C_8H_{13}ClN_2O_4$: Calcd: C, 40.50, H, 5.49, N, 11.83, Found: C, 37.46; H, 5.59, N, 12.90.

The compounds listed in Table I, below, were also prepared by the above procedures.

TABLE I

ELEMENTAL ANALYSES AND MELTING POINTS OF OXIME N—METHYL-N—alpha-CHLOROACETYL-CARBAMATES $$R=N-O-\underset{\underset{}{\overset{O}{\|}}}{C}-\underset{\underset{CH_3}{|}}{N}-\overset{O}{\overset{\|}{C}}-CH_2-Cl$$

| Structure R | m.p. °C | Calculated C | Calculated H | Calculated N | Found C | Found H | Found N |
|---|---|---|---|---|---|---|---|
| 2-ylidine-1,4-dithiane | 131–131 | 33.98 | 3.92 | 9.90 | 34.12 | 4.66 | 9.67 |
| 2-ylidine-5,5-dimethyl-N—methyl-1,3-thiazolidin-4-one | 149–150 | 39.12 | 4.58 | 13.65 | 39.13 | 4.64 | 13.65 |
| 4-ylidine-5-methyl-1,3-oxathiolane | — | 36.02 | 4.15 | 10.49 | 35.43 | 4.43 | 10.24 |
| $CH_3-\underset{\underset{CH_3}{|}}{\overset{\overset{CH_3}{|}}{C}}-CH=$ | — | 46.05 | 6.44 | 11.93 | 47.77 | 7.49 | 12.83 |
| $\underset{CH_3-ON}{CH_3-C}\overset{\|}{=}\underset{CON(CH_3)_2}{C=}$ | 63–65 | 41.18 | 5.34 | 17.46 | 40.74 | 5.60 | 17.41 |
| $CH_3O\overset{\overset{O}{\|}}{C}-\underset{\underset{CN}{|}}{C}=$ | oil | 36.72 | 3.08 | 16.06 | 35.23 | 4.01 | 15.79 |
| $CH_3SCH_2-\underset{\underset{CH_3}{|}}{C}=$ | oil | 38.01 | 5.18 | 11.08 | 37.10 | 5.26 | 11.85 |
| $(CH_3)_2CHS-CH_2-\underset{\underset{CH_3}{|}}{C}=$ | oil | 42.77 | 6.10 | 9.98 | 45.02 | 6.48 | 9.41 |
| $CH_3-\underset{\underset{OC_2H_5}{|}}{C}=$ | 69–71 | 40.50 | 5.49 | 11.83 | 37.46 | 5.59 | 12.90 |

Illustrative of my invention are the following compounds:

2-methyl-2-nitropropionaldoxime N-chloroacetyl-N-methylcarbamate;

4-cyano-2,2-dimethylbutyraldoxime N-chloroacetyl-N-methylcarbamate;

2-methoxy-2-methylpropionaldoxime N-chloroacetyl-N-methylcarbamate;

1-methylthio-3,3-dimethyl-2-butanoneoxime N-chloroacetyl-N-methylcarbamate;

3-methylthio-2-butanoneoxime N-chloroacetyl-N-methylcarbamate;

3-methylsulfonyl-2-butanone oxime N-chloroacetyl-N-methylcarbamate;

2,2-bismethylthiopropionaldoxime N-chloroacetyl-N-methylcarbamate;

1-methoxyacetaldoxime N-chloroacetyl-N-methylcarbamate;

1-cyclopropylacetaldoxime N-chloroacetyl-N-methylcarbamate;

3-isopropyl-1,3-thiazolidin-4-one-2-oxime N-chloroacetyl-N-methylcarbamate;

5,5-dimethyl-2-dicyanomethylidene-1,3-dithiolan-4-oxime N-chloroacetyl-N-methylcarbamate; thiophane-2-oxime N-chloroacetyl-N-methylcarbamate; and 5-methyl-1,3-dithiolane-4-oxime N-chloroacetyl-N-methylcarbamate.

The oxime N-alkyl-N-α-haloacyl-carbamates of this invention were evaluated to determine their pesticidal activity against selected aphids, mites, worms, beetles and houseflys.

Solutions or suspensions of the test compounds were prepared by dissolving 375 mg. of compound in 7.5 ml of dimethylformamide. To this was added 15 ml of acetone in which had been dissolved 37.5 mg (10 percent of the weight of the compound) of an alkylphenoxy polyethoxyethanol surfactant, as an emulsifying or dispersing agent. The resulting solution was mixed into 52.5 ml of water to give roughly 75 ml of a suspension containing the compound in finely divided form. The thus-prepared stock suspension contained 0.5 percent by weight of compound. The concentrations in parts per million by weight employed in the tests described hereinbelow were obtained by appropriate dilutions of the stock suspension with water. Pesticidal activity was determined using the procedures set forth below.

BEAN APHID FOLIAGE SPRAY TEST

Adults and nymphal stages of the bean aphid (*Aphis fabae* Scop.) reared on potted dwarf nasturtrium plants at 68°–70° F. and 50±5% relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids were placed on a revolving turntable and sprayed with 100–110 milliliters of test compound forumlation by use of a spray gun set at 40 psig air pressure. This application, which lasted 25 seconds, was sufficient to wet the plants to run-off. As a control, 100–110 milliliters of a water-dimethylformamide-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 68°–70° F. and 50±5 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

MITE FOLIAGE SPRAY TEST

Adults and nymphal stage of the two-spotted mite (*Tetranychus urticae* Koch), reared on Tendergreen bean plants at 80±5% relative humidity, were the test organisms. Infested leaves from a stock culture were placed on the primary leaves of two bean plants 6 to 8 inches in height, growing in a 2½ inch clay pot. A sufficient number of mites for testing (150–200) were transferred from the excised leaves to the fresh plants in a period of 24 hours. Following the 24 hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a spray gun set at 40 psig. air pressure. This application, which lasted 25 seconds, was sufficient to wet the plants to run-off. As a control, 100–110 milliliters of a water solution containing acetone, dimethylformamide and emulsifier in the same concentrations as the test compound formulation, but containing no test compound, were also sprayed on infested plants. The sprayed plants were held at 80±5% relative humidity for 6 days, after which a mortality count of motile forms were made. Microscopic examination for motile forms were made on the leaves of the test plants. Any individual which was capable of location upon prodding was considered living.

SOUTHERN ARMYWORM LEAF SPRAY BAIT TEST

Larvae at the southern armyworm (*Spodoptera eridania*, (Cram.)), reared on Seiva Pole lima bean plants at a temperature of 80°±5° F. and a relative humidity of 50±5%, constituted the test insects.

The test compounds were formulated by diluting the stock suspension with water to give a suspension containing 500 parts of test compound per million parts of final formulation. Potted Seiva Pole lima bean plants in the primary leaf stage and of standard height and age were placed on a revolving turntable and sprayed with 100–110 milliliters of test compound formulation by use of a spray gun set at 40 psig air pressure. This application, which lasted 25 seconds, was sufficient to wet plants to run-off. As a control, 100–110 milliliters of water-dimethylformamide-acetone-emulsifier solution containing no test compound were also sprayed on infested plants. When dry, the paired leaves were separated and each one was placed in a 9 centimeter petri dish lined with moistened filter paper. Five randomly selected larvae were introduced into each dish and the dishes were closed. The closed dishes were labeled and held at 80°–85° F. for three days. Although the larvae could easily consume the whole leaf within 24 hours, no more food was added. Larvae which were unable to move the length of the body, even upon stimultion by prodding, were considered dead. Percent mortality was recorded for various concentration levels.

MEXICAN BEAN BEETLE LEAF SPRAY TEST

Fourth instar larvae of the Mexican bean beetle (*Epilachna varivesti*, Muls.), reared on Seiva Pole lima bean plants at a temperature of 80°±5° F. and 50±5% relative humidity, were the test insects.

The test compounds were formulated by diluting the stock suspension with water to give a suspension containing 500 parts of test compound per million parts of final formulation. Seiva Pole lima bean plants in the primary leaf stage and of standard height and age were placed on a revolving turntable and sprayed with 100–110 milliliters of test compound formulation by use of a spray gun set at 40 psig air pressure. This application, which lasted 25 seconds, was sufficient to wet plants to run-off. As a control, 100–110 milliliters of a water-dimethylformamide-acetone-emulsifier solution containing no test compound were also sprayed on infested plants. When dry, the paired leaves were separated and each was placed in a 9 centimeter petri dish lined with moistened filter paper. Five randomly selected larvae were introduced into each dish, and the dishes were closed. The closed dishes were labeled and held at a temperature of 80°±5° F., for 3 days. Although the larvae could easily consume the leaf within 24 to 48 hours, no more food was added. Larvae which were unable to move the length of the body, even upon stimulation, were considered dead.

FLY BAIT TEST

Four to six day old adult house flies (*Musca domestica*, L.), reared according to the specifications of the Chemical Specialities, Manufacturing Association (Blue Book, McNair-Dorland Co., New York 1954; pages 243–244, 261) under controlled conditions of 80°±5° F. and 50±5% relative humidity, were the test insects. The flies were immobilized by anesthetizing with carbon dioxide and 25 immobilized individuals, males and females, were transferred to a cage consisting of a standard food strainer about 5 inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the good strainer prior to admitting the anesthetized flies. The caged flies were allowed to feed on the bait for 24 hours, at a temperature of 80°±5° F. and a relative humidity of 50±5%.

Flies which showed no sign of movement on prodding were considered dead.

Each compound was assigned a rating for each pest based on the following criteria:
A=excellent control at 500 ppm;
B=partial control at 500 ppm;
C=no control at 500 ppm.

It is to be understood that those compounds which exhibited only partial control or even no control at 500 ppm will exhibit greater control at higher levels of application.

The following tables, Table II and Table III, illustrates the broad insecticidal and miticidal activity of the N-α-haloacylated oximes of this invention an in particular the excellent insecticidal properties of these compounds.

the desired dispersion of the toxicant in the spray so that rain does not re-emulsify the toxicant after it is applied to the plant and wash it off the plant. Non-ionic, anionic, amphoteric, or cationic dispersing and emulsifying agents may be employed, as for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersed agents as well as lignosulfonates can be included.

The required amount of the toxicants contemplated

TABLE II

PESTICIDAL ACTIVITY OF ACYLIC OXIME N—alpha-HALOACETYL CARBAMATES $$R^2-C(=N-O-C(=O)-N(CH_3)-C(=O)-CH_2-Cl)-R^3$$

| Compound Number | Structure R$^2$ | R$^3$ | Bean Aphid | Adult Mites | Southern Armyworm | Mexican Bean Beetle | Housefly |
|---|---|---|---|---|---|---|---|
| 1 | 2-methylthio-2-propyl | hydrogen | A | A | B | A | A |
| 2 | 2-methylsulfonyl-2-propyl | hydrogen | A | C | C | A | A |
| 3 | 2-cyano-2-propyl | hydrogen | A | A | A | A | A |
| 4 | 1-methyloximinoethyl | N,N—dimethyl-aminocarbonyl | A | C | C | B | A |
| 5 | methylthiomethyl | methyl | B | C | C | C | A |

TABLE III

PESTICIDAL ACTIVITY OF CYCLIC OXIME N—alpha-HALOACETYL CARBAMATES $$R=N-O-C(=O)-N(CH_3)-C(=O)-CH_2-Cl$$

| Compound Number | Structure R | Bean Aphid | Mites | Southern Armyworm | Mexican Bean Beetle | Housefly |
|---|---|---|---|---|---|---|
| 6 | 2-ylidine-1,4-dithiane | A | B | A | A | A |
| 7 | 4-ylidine-5-methyl-1,3-oxathiolane | A | C | A | A | A |
| 8 | 2-ylidine-5,5-dimethyl-N—methyl-1,3-thiazolidin-4-one | C | C | A | A | B |

Pesticidal compositions comprising an acceptable carrier and a pesticidally acceptable amount of such compounds may be provided and applied in methods for controlling insects or mites according to well established procedures. Pesticidal compositions containing such compounds as the active agent will usually comprise a carrier and/or diluent, in either liquid or solid form.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene, followed by dispersing the agents in water with the acids of a suitable surface active, emulsifying and dispersing agents.

The choice of dispersing and emulsifying agents and the amount employed depends on by the nature of the composition and the ability of the agent to facilitate the dispersion of the toxicant. Generally it is desirable to use as little of the agent as is possible, consistent with herein can be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides of this invention control the population of insects, mites and mite and insect ova upon plants or other material to which the pesticides are applied. Generally, when used in sufficient amout to kill or repel the insects, they do not burn or injure the plant. The toxicants are compatible with substantially any other constituents of the spray schedule, and they can be used in the soil, upon the seeds, or the roots of plants without injuring either the seeds or roots of plants.

They can also be used in combination with other pescicidally active compounds.

I claim:

1. Compounds having the structure:

$$A\underset{}{\bigcirc}C=N-O-\underset{}{\overset{O}{\overset{\|}{C}}}-\underset{R'}{\overset{}{N}}-\underset{R''}{\overset{O}{\overset{\|}{C}}}-CH-X$$

wherein:

R' is $C_{1-4}$ alkyl;

R" is hydrogen or $C_{1-4}$ alkyl;

X is chlorine, fluorine or bromine; and

A together with the carbon atom forms a cyclic radical selected from 2-ylidine-1,4-dithiane, 2-ylidine-1,3-dithiane, 4-ylidine-1,3-dithiolane and 2-ylidine-1,3-dithiolane; wherein the carbon atoms of said cyclic radical may be $C_{1-4}$ alkyl substituted.

2. A compound in accordance with claim 1 wherein said R' is methyl, said R" is hydrogen and said X is chlorine.

3. In accordance with claim 1 the compound 1,4-dithiane-2-oxime N-methyl-N-chloroacetylcarbamate.

4. An insecticidal and miticidal composition comprising an insecticidally or miticidally effective amount of a compound according to claim 1 and and acceptable carrier.

5. A compound in accordance with claim 4 wherein said active toxicant is the compound 1,4-dithiane-2-oxime N-methyl-N-chloroacetylcarbamate.

6. A method for controlling insects or mites comprising subjecting the insects or mites to an insecticidally or miticidally effective amount of a compound according to claim 1.

7. A method in accordance with claim 6 wherein said compound is the compound 1,4-dithiane-2-oxime N-methyl-N-chloroacetylcarbamate.

* * * * *